United States Patent [19]

Kaplan

[11] 4,283,578

[45] Aug. 11, 1981

[54] PROCESS FOR MAKING GLYCOL

[75] Inventor: Leonard Kaplan, Charleston, W. Va.

[73] Assignee: Union Carbide Corporation, New York, N.Y.

[21] Appl. No.: 152,608

[22] Filed: May 23, 1980

[51] Int. Cl.³ .............................................. C07C 31/20
[52] U.S. Cl. ............................. 568/852; 260/429 R; 260/429.7; 568/861; 556/451; 556/489
[58] Field of Search ................................. 568/852, 861

[56] References Cited

U.S. PATENT DOCUMENTS

| | | | |
|---|---|---|---|
| 2,626,272 | 1/1953 | Speier | 568/852 |
| 4,076,758 | 2/1978 | Owsley et al. | 568/852 |

FOREIGN PATENT DOCUMENTS

| | | | |
|---|---|---|---|
| 533377 | 11/1956 | Canada | 568/861 |
| 50-53349 | 12/1975 | Japan | 568/858 |
| 597117 | 3/1978 | Switzerland | 568/852 |

*Primary Examiner*—Joseph E. Evans
*Attorney, Agent, or Firm*—George A. Skoler

[57] ABSTRACT

This invention is concerned with producing ethylene and/or 1,2-propylene glycol by the reaction of a noncyclic oxymethylene compound formed by the hydration or acetalization of formaldehyde with a compound containing one or more of silicon, germanium and tin bonded therein which functions as an addend in a photochemically or thermally induced radical reaction, to form a 1,2-dioxyethylene containing compound, and cleaving such 1,2-dioxyethylene containing compound to form the glycol thereof.

6 Claims, No Drawings

PROCESS FOR MAKING GLYCOL

This invention is directed to the production of glycol from non-cyclic oxymethylene compounds formed by the hydration or acetalization of formaldehyde. More particularly this invention is directed to the formation of glycols by the reaction of such non-cyclic oxymethylene compounds with compounds containing one or more of silicon, germanium and tin bonded therein.

The following prior art describes the reaction of aldehydes or ketones with organo tin, organo silicon and organo germainium compounds. Many describe coupling reactions involving aldehydes or ketones. None of these references describe coupling reactions involving formaldehyde or coupling reactions involving formaldehyde or the production of simple glycols. (Neumann, infra, describes, for example, 2,3-butanediol diacetate).

W. P. Neumann, in a variety of publications, has described the reaction of aldehydes, such as acetaldehyde, and ketones, such as acetone, with organo tin compounds to produce products which are represented, for convenience sake, as dioxastannolanes. Particular reference is made to Neumann and Schwarz, Agnew. Chem. Internat. Edit., 14, 812 (1975); Grugel, Neumann, and Seifert, Tet. Lett., 2205 (1977); Grugel, Neumann, Sauer, and Seifert, Tet. Lett. 2847 (1978); and Neumann in The Organometallic and Coordination Chemistry of Germanium, Tin and Lead, Editors: Gielen and Harrison, 1978, Georgi Publishing Company, Switzerland, pages 51–74. See also, Horowitz and Calvert, Int. J. Chem. Kinet, 10, 713 (1978); Cooper, Hudson, and Jackson, J.C.S. Perkin II, 1933 (1973); Mironov, Berliner, and Gar, Zh. Obshch. Khim., 38, 1900 (1968); 39, 2701 (1969); Massol, Barrau, Rivière and Satgé, J. Organometal. Chem., 30, 27 (1971); Mironov, Berliner, Gar, and Ponomareva, Zh. Obshch. Khim., 40, 109 (1970); Bockharev, Vyazankin, Bochkarev, and Razuvaev, J. Organometal. Chem., 110, 149 (1976); Bott, Organometal. Chem. Rev. (B), 7, 109 (1971); Ritter and Lindemann, II$^e$ Symp. Internat. sur la Chemie des Composés Organique du Silicium, Resumes des Communications, Bordeaux, 1968, page 157; Beaumont, Eaborn, and Jackson, J. Chem. Soc. (B) 1624 (1970); Janzen, Rodesiler, and Willis, Chem. Comm. 672 (1966); Sitzki and Ruehlmann, Z. Chem., 8, 427 (1968); Becker, J. Org. Chem., 34, 2469 (1969); Hillgaertner, Neumann, and Schroeder, Ann., 586 (1975); Neumann, Schroeder, and Ziebarth, Ann., 2279 (1975); Louis and Urry, Tet. Lett., 3295 (1968); Frainnet, Pure Appl. Chem., 19, 494 (1969); Glushkova, Kharitonov, Tregubova, Zh. Obshch. Khim., 43, 1075 (1973); Frainnet and Bourhis, Bull. Soc. Chim. France, 2134 (1966); Dedier, Bourhis, Siegfried, and Frainnet, Bull. Soc. Chim. France, 2699 (1965); Frainnet and Bourhis, Bull. Soc. Chim. France, 574 (1965); Frainnet, Pure Appl. Chem., 19, 494 (1969); Frainnet, Bourhis, Simonin, and Moulines, J. Organometal. Chem., 105, 17 (1976); Glushkova and Kharitonov, Zhur, Obshch, Khim., 45, 2018 (1975); Glushkova and Kharitonov, Izv. Akad. Nauk SSSR, 88 (1967); Johnson and Gladysz, J. Am. Chem. Soc., 101, 6433 (1979); Neumann and Neumann, J. Organometal. Chem., 42, 277 (1972).

Ethylene glycol is commercially produced by the hydrolysis of ethylene oxide which in turn is generated by the oxidation of ethylene, typically by the reaction of ethylene and oxygen over a silver containing catalyst. The reaction is a heterogeneous gas phase reaction. Other processes (non-commercial) for making glycol involve reactions of carbon monoxide with hydrogen or formaldehyde, typically in the presence of a precious metal catalyst. Such processes are described as being operated at pressures as low as 1 atmosphere to 3400 atmospheres.

This invention is directed to producing ethylene glycol and/or propylene glycol by reacting a non-cyclic oxymethylene compound formed by the hydration or acetalization of formaldehyde with a compound containing one or more of silicon, germanium and tin bonded therein, to form a 1,2-dioxyethylene containing compound, and cleaving such 1,2-dioxyethylene containing compound to form the glycol thereof.

The non-cyclic oxymethylene compounds used in the practice of this invention include the hydration products and acetalization products of formaldehyde, such as are present in formalin and paraformaldehyde. It should be understood that by the term acetalization it is intended to include both the hemiacetal as well as the acetal of formaldehyde. Moreover, this invention does not exclude acetals formed by the reaction of one or more of a variety of alcohols with formaldehyde. For example, the hemiacetal and acetal of formaldehyde and methanol are excellent non-cyclic oxymethylene compounds to be employed in the practice of this invention. Included as a reactant to be provided with such non-cyclic oxymethylene compounds is acetaldehyde. It can be present in amounts up to an amount equivalent to the amount of oxymethylene present. The co-reaction or co-coupling of oxymethylene with acetaldehyde results in the formation of 1,2-propylene glycol.

The silicon, germanium and tin compounds which are reactable with the non-cyclic oxymethylene compound to effect the process of this invention are any of such compounds which function as an addend in a photochemically or thermally induced radical reaction*. More narrowly defined, such compounds introduced per se, or formed in situ during the course of this process, should contain the elements silicon, germanium and/or tin bonded to at least one of the same elements (i.e., silicon, germanium or tin), or carbon or hydrogen or a combination of them. In a more restrictive sense, but not more definitive than the preceding, the compounds can contain a bond to one or more of silicon, germanium and/or tin which has a bond dissociation energy less than or equal to 80 kilocalories per mole, preferably less than or equal to 70 kilocalories per mole. This description of the compounds containing one or more of silicon, germanium and tin is not intended to imply a mechanism for the process of this invention as a consequence of the compounds' capabilities in functioning as an addend in a photochemically or thermally induced radical reaction. Nor is it intended to imply a mechanism because of the above definition which specifies the kind of bond between such elements as silicon, germanium and tin, and bond strengths. However, it may be that the functional characteristics of the compounds which contain one or more of silicon, germanium and tin play a role in the mechanism of the reaction but to assume that such is a fact would be improper. However, it is important to recognize that although the mechanism by which the process of this invention is effected cannot be postulated as dependent upon the function of the compound to act as an addend in a photochemically or thermally induced radical reaction, this capability does delineate quite effectively those compounds which are encompassed to be used in the practice of the process of this invention.

*Citations showing that organosilicon, germanium and tin compounds can function as addends in radical reactions:
E. L. Lukevits and M.G. Voronkov, "Organic Insertion Reactions of Group IV Elements," Plenum Publishing Corp., 1966.
"Organometallic Compounds," ed. M. Dub, vol. II - "Compounds of Germanium, Tin, and Lead," 2nd ed., ed. R. W. Weiss, Springer-Verlag, 1967.
"Organometallic Compounds," ed. M. Dub, vol. II - "Compounds of Germanium, Tin, and Lead," 2nd ed., first supplement, 1973.
"Organotin Compounds," ed. A. K. Sawyer, vols. 1-3, Marcel Dekker, 1971–1972.
"Organometallic Compounds of the Group IV Elements," ed. A. G. MacDiarmid, vol. 1, "The Bond to Carbon," ed. A. G. MacDiarmid Parts I and II, Marcel Dekker, 1968.
M. Lesbre, P. Mazerolles, and J. Satgé, "The Organic Compounds of Germanium," Wiley, 1971.
W. P. Neumann, "The Organic Chemistry of Tin," Wiley, 1970.
R. C. Poller, "The Chemistry of Organotin Compounds," Academic Press, 1970.
F. Glockling, "The Chemistry of Germanium," Academic Press, 1969.
V. Bažant, V. Chvalovský, and J. Rathouský, "Organosilicon Compounds," vol. 1, "Chemistry of Organosilicon Compounds," V. Bažant and V. Chvalovsky, Academic Press, 1965.

It is also important to recognize that the kind of substitution on the silicon, germanium and/or tin plays an insignificant role in the compound's suitability to be employed effectively in the process of this invention. A large or small organic radical, aromatic or aliphatic, monomeric or polymeric, functional containing or not, bonded to such elements plays an important role in defining the amount of such compound to be employed in the process and the conditions under which the process is operated, but not in defining the compound's operativeness in practicing the process.

The variety of such compounds usable in the practice of this invention is obviously vast, but such variety demonstrates the accuracy of the definition of the compounds as a basis for their selection. Specific compounds which to date have been successfully employed in process of this invention are the following:

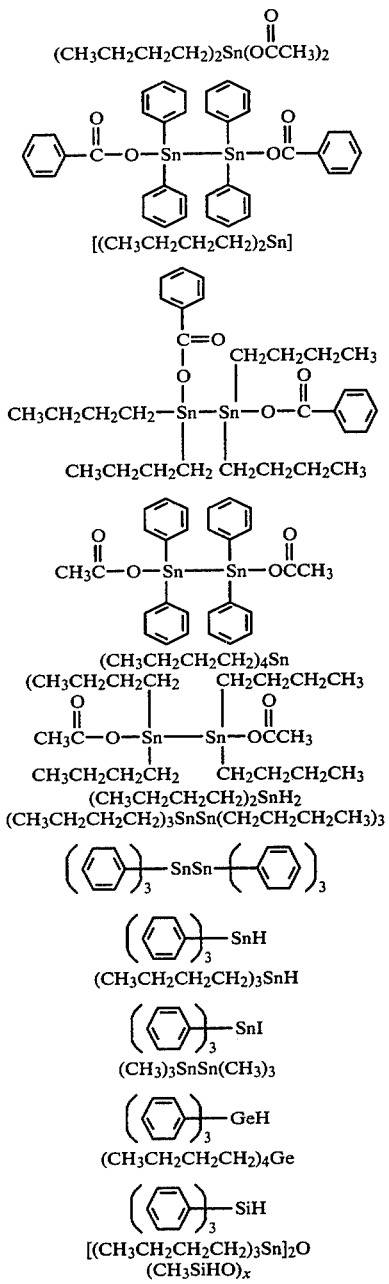

The process of this invention can be carried out in a homogeneous or heterogeneous reaction mixture. The reactants can be in the vapor, liquid or solid phase with the proviso that at least one of the reactants, viz. the non-cyclic oxymethylene compound and the metal-containing compound, where the metal is one of silicon, germanium, and tin, is in either the liquid or gas phase. If, for example, the non-cyclic oxymethylene compound is in the liquid phase and the metal compound in solid or an insoluble liquid or vice versa, the reaction is believed to occur in a homogeneous phase resulting from the solubilization under reaction conditions of either insoluble non-cyclic oxymethylene or insoluble metal compound, or both, or the solubilization of decomposition products of either which are precursors to glycol product formation or are the byproducts of the reaction. One or more of the reactants can be dissolved in a solvent when the reaction is carried out in a homogeneous or heterogeneous phase.

Solvents suitable in the practice of this invention are any material liquid under the reaction conditions which dissolves at least one of the reactants and is essentially inert to the reaction. A solvent is essentially inert to the reaction when it does not prevent the reaction from occurring. This does not mean that the solvent is incapable of entering into a reaction concurrently with the reaction of choice. However, it is impractical to use solvents that so severely compete for one or more of the reactants as to adversely affect the economic viability of this process. This is not the case when one of the reactants is a solvent in the reaction.

Illustrative of suitable solvents are, e.g., ketones such as acetone, methyl ethyl ketone, dibutyl ketone, acetophenone, diphenyl ketone and acetylacetone; hydrocarbons such as benzene, hexane, undecane, naphthalene, t-butyl benzene, tetralin, decalin, and the like; ethers such as dimethyl ether, diethyl ether, di-n-butyl ether, diphenyl ether, and the like; sulfones and sulfoxides such as dimethyl sulfoxide and sulfolane; alcohols such as methanol, ethanol, stearyl alcohol, cyclohexanol, and the like; esters such as ethyl acetate, isopropyl acetate, methyl propionate, n-butyl acetate, and the like; amides such as N,N-dimethyl formamide, N,N-diethylacetamide, and the like; lactones such as, butyrolactone, caprolactone and the like; nitriles such as acetonitrile, butyronitrile, and the like.

The reaction may be carried out at extremely low to extremely high temperatures. The minimum temperature is that at which the reaction will proceed and the maximum temperature is that at which one or more of the reactants or solvents combust, detonate or severely decompose (prematurely). The temperatures at which the reaction can be carried out range between about −40° C. to about 400° C. or higher, preferably between about 20° C. to about 350° C.

The pressures at which the reaction can be effected are not narrowly critical. The reaction can be carried out under subatmospheric to superatmospheric pressures. If the solvent is non-volatile under subatmospheric pressures, the pressure employed can be as low as 1 micron mercury pressure, or lower. The maximum pressure is based upon the pressure needs imposed by the reactants used and the other conditions of the reaction. For example, pressures as high as 50 atmospheres or greater can be employed; for example a gas-phase process running at such pressures over a heterogeneous catalyst can be envisioned.

The reaction is initiated by providing conditions where the reactants reside which could cause the compound containing one or more of silicon, germanium and tin to function as an addend in a photochemically or thermally induced radical reaction. With respect to this statement, the previously made caveat about mechanism is repeated. In the usual case, the reaction will be initiated under conditions which effect a photochemical or thermally-induced reaction between the non-cyclic oxymethylene compound and the metal compound or the reaction of the metal compound to form an intermediate which reacts with oxymethylene compound to produce the 1,2-dioxyethylene product. Light can be a source of reaction initiation. One may employ visible light, ultraviolet light, and combinations thereof. Other radical initiators such as peroxides, hydroperoxides, peresters, azo compounds, and the like, can be used to initiate the reaction. We recognize that, in those experiments which involve use of a free radical initiator, the initiator and the organometallic reagent may react with each other under conditions milder than those necessary for formaldehyde to react or for unassisted thermal decomposition of the initiator. Of course, none of these need be employed since heat alone will initiate the reaction. Temperatures as low as 20° C. to about 400° C. and higher, can be employed to initiate the reaction.

The time needed to carry out the process can be as low as fractions of a second to hours, even to days. Heterogeneous vapor phase reactions may be run in less than a second, and some heterogeneous liquid phase reactions require hours before the process is completed.

The 1,2-dioxyethylene compounds resulting from the aforedefined process are precursors of the glycol product.

They are believed to be 1,2-dioxyethylene compounds of the following formula:

—OCH$_2$CHRO—, where R is hydrogen or methyl, and the free valences of the terminal oxygen may be bonded directly to at least one of silicon, germanium and tin. It is well known that such compounds can be cleaved by a number of procedures which will directly result in producing the glycol or a precursor which easily provides the glycol.

There are a number of general procedures for converting such 1,2-dioxyethylene compounds to the corresponding glycols. One involves hydrolysis, another involves hydrogenolysis, and still another involves hydrostannolysis.

Hydrolysis involves the water treatment of the 1,2-dioxyethylene compound. Hydrogenolysis involves the addition of hydrogen with accompanying bond breakage.

Hydrostannolysis involves the reaction of a compound containing a tin hydrogen bond to break the tin oxygen bond of the 1,2-dioxyethylene tin compound; the 1,2-dioxyethylene moiety is replaced by tin, the hydrogen serving to cap the 1,2-dioxyethylene radical to form the glycol. (See W. P. Neumann, J. Pedain, and R. Sommer, Ann., 694, 9(1966) and W. P. Neumann and B. Schneider, Angew. Chem. Internat. Edit., 3, 751 (1964) for the following reaction:

$$R_2Sn(OR')_2 + R_2SnH_2 \rightarrow 2R'OH + 2/x(R_2Sn)_x \quad (1)$$

Hydrolysis is a common process for cleaving metal-oxygen-carbon linkages and the resulting metal is left bonded to —OH and the —oxygen-carbon portion is capped by hydrogen. Acids and bases are known to speed up such reactions. Alcoholysis is another version of hydrolysis except that alcohol replaces at least part of the water and the metal is left bonded to alkoxide derived from the alcohol.

Hydrogenolysis can be effected by the cleavage of the 1,2-dioxyethylene compound with molecular hydrogen or with hydrides such as lithium aluminum hydride, boron hydride, and the like. See E. J. Corey and A. Venkateswarlu, J. Am. Chem. Soc., 94, 6190 (1972).

Reaction (1) above offers the basis for the regeneration of tin to a form desirable in effecting this process. Thus the following cyclic reaction system is believed feasible and enhances the possibility of the process of this invention to be a portion of a continuous cyclic process.

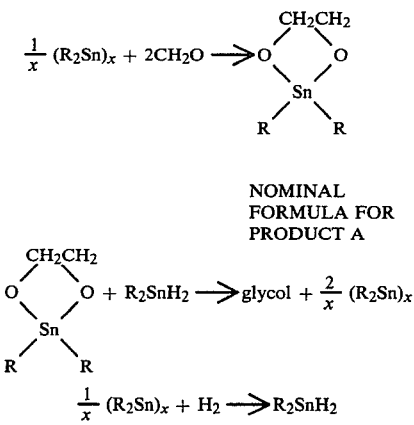

NOMINAL FORMULA FOR PRODUCT A

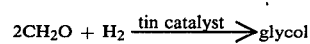

In summary:

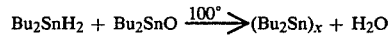

In the foregoing reactions, the 2 moles of formaldehyde can be replaced by one mole of formaldehyde and one mole of acetaldehyde to generate instead 1,2-propylene glycol.

MATERIALS

(Bu$_2$Sn)$_x$

This highly air-sensitive material was prepared as follows [A. K. Sawyer, U.S. Pat. No. 3,322,801 (1967)]:

Its nmr spectrum showed no extraneous absorptions. A solution of it in benzene was stirred in air for 48 hrs. The solvent was evaporated, leaving a white solid, mp <300°. Anal. (Galbraith Labs, Knoxville, Tenn.) Calcd for Bu$_2$SnO: Sn, 47.69. Found: 47.61

AcOBu$_2$SnSnBu$_2$OAc

This highly air-sensitive material was prepared as follows [A. K. Sawyer and H. G. Kuivila, J. Org. Chem. 27, 610 (1962)]:

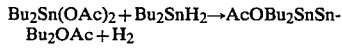

Mp −3.5° to −2° (lit.[8] −7° to −4°). It was treated with Br$_2$ in CCl$_4$[8] and the resulting solution pumped to dryness to give 100% AcOBu$_2$SnBr [mp 65°–65.5° (lit[8] 66°-7°); nmr (CCl$_4$): tau=7.94 (s,3.0H), 8.0-9.3(m, 18.0H)]. Anal. (Galbraith) Calcd. for C$_{20}$H$_{42}$O$_4$Sn$_2$: C,41.14; H,7.25. Found: C,41.48; H,7.24.

Sources of Formaldehyde

Trioxane is only formally a trimer of formaldehyde; its chemistry is often very different. It was recrystallized from hexanes and then distilled[1]; mp 63°-4°. α-Polyoxymethylene was generated from paraformaldehyde[2]. Commercial (Baker) 38% formalin was used without further treatment.

Miscellaneous Materials

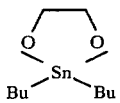

(formal structure) (ref. 3) [mp 224°-8°; nmr (CDCl$_3$): =6.36(s,4.0H), 8.0-9.3(m,20H)], PhCO$_2$Ph$_2$SnSnPh$_2$O$_2$CPh (ref. 4) [mp 180°-181.5° (d)], and PhCO$_2$Bu$_2$SnSnBu$_2$O$_2$CPh (ref. 5) [nmr (CD$_3$COCD$_3$): aryl (m, 10.0H), alkyl (m,38H)] were prepared by use of literature procedures.

SnCl$_2$ (480 g) was purified by slow addition, with exclusion of water, to 400 g of freshly-distilled acetic anhydride. The mixture was stirred for 1 hr. then filtered, and the solids washed with 2×120 ml of dry ether and then dried under vacuum.

Bu$_2$SnH$_2$ was distilled to give material, bp 73°/3 mm, whose nmr spectrum (benzene) consisted of absorptions 153 cps (m, 1.68H) and 320-610 cps (m, 18.0H) upfield from benzene. 8 Note that $^{117}$Sn and $^{119}$Sn are present in natural abundances of 7.6 and 8.6, respectively, and that J($^{117}$Sn-H)≃1610 cps and J($^{119}$Sn-H)=1680 cps].

AcOPh$_2$SnSnPh$_2$OAc was prpared[8] from diphenyltin dihydride[6]. Nmr (CD$_2$Cl$_2$): multiplet (20.3H) 115-155 cps downfield from CHDCl$_2$ and singlet (6.0H) 188 cps upfield. Anal. Calcd for C$_{28}$H$_{26}$O$_4$Sn$_2$: C, 50.66; H, 3.95. Found: C, 50.17; H, 3.67.

Ph$_3$SnH was distilled to give material, bp~165°/0.3 mm.

Ph$_3$SnI was prepared from Ph$_3$SnH and iodobenzene[7]. Mp 116-120°.

References (1) V. Jaacks+ W. Kern, Makromol. Chem. 52, 37 (1962)
(2) F. Walker, J. Am. Chem. Soc., 55, 2821 (1933)
(3) W. J. Considine, J. Organometal. Chem., 5, 263 (1966)
(4) G. J. Del Franco, P. Resnick, and C. R. Dillard, ibid., 4, 57 (1965)
(5) A. K. Sawyer and H. G. Kuivila, U.S. Pat. No. 3,083,217 (1963)
(6) H. G. Kuivila, A. K. Sawyer, and A. G. Armour, J. Org. Chem., 26, 1426 (1961)
(7) L. A. Rothman and E. I. Becker, J. Org. Chem., 25, 2203 (1960).
(8) A. K. Sawyer + H. G. Kuivila, J. Org. Chem. 27, 610 (1962)

GENERAL PROCEDURES

Unless indicated otherwise in the examples, the initial reactions between the metal compound and the non-cyclic oxymethylene reactant and subsequent treatment of the reductively coupled reaction product, were effected substantially following the general procedures described hereinbelow as Procedures I-A to I-D and Procedures II-A to II-C, respectively. The particular combination of procedures employed in any individual example is indicated in the specific description of the examples. In each procedure, all manipulative steps including work-up procedures were effected in the absence of air by use of a combination of dry box, Schlenk and vacuum line techniques.

I. Procedures For the Reductive Coupling Reaction

Procedure I-A—Photochemical Initiation Using Sunlamp

In accordance with this procedure, the reaction mixture containing the metal compound, source of non-cyclic oxymethylene (and acetaldehyde reactant when used) and solvent, was irradiated with a sunlamp under a variety of temperature/reaction time conditions. Depending upon the volume of the total reaction mixture, the reaction was effected in one or more nmr tubes (5 mm. O.D.) to which the solvent, metal compound and oxymethylene reactant were charged sequentially. When more than one tube was used, the components was charged to each tube in approximately equal volumetric portions. The tube(s) was sealed under vacuum and irradiated with a General Electric 275W sunlamp equipped with a reflector. The temperature was measured by use of a thermometer fastened to the tube(s), the bulb of the thermometer being adjacent to the solution in the tube. The reaction temperature was controlled at the desired level by adjustment of the distance between the lamp and the tube(s), or by fan cooling as required. For example, placing the lamp about 1 ¾ inches from the tube(s), maintained the temperature at about 96° to 99° C. Where indicated in the detailed description of the examples, the progress of the reaction was monitored by use of nmr spectroscopy at various intervals. The reaction mixture was then treated in accordance with one or more of the procedures described hereinbelow as Procedures II-A, II-B, II-C, or as otherwise indicated in the specific description of the examples.

Procedure I-B—Photochemical Initiation Using Mercury Lamp

In accordance with this procedure, the initial reaction mixture containing the metal compound, the source of non-cyclic oxymethylene (and acetaldehyde reactant when used) and solvent, was irradiated with a mercury lamp under a variety of temperature/reaction time conditions. The reaction was carried out in an nmr tube (5 mm. O.D.) to which the solvent, metal compound and oxymethylene reactant were charged sequentially. The tube was then sealed under vacuum and irradiated with a Hanovia 450W medium pressure mercury lamp equipped with a reflector. The temperature was measured by use of a thermometer fastened to the outside of the tube, the thermometer bulb being adjacent to the solution in the tube. The reaction temperature was controlled at the desired level by adjustment of the distance between the lamp and the tube, or by fan cooling as required. For example, fan cooling of the tube while positioned about 5 inches from the lamp maintained the tube temperature at about 31° C. Further, placing the lamp about 2 inches from the tube maintained the temperature at about 80° C. without fan cooling. The progress of the reaction was monitored after each hour, by use of nmr spectroscopy. The reaction mixture was then treated in accordance with one or more of the procedures described hereinbelow as Procedures II-A, II-B, II-C, or as otherwise indicated in the specific description of theexamples.

Procedure I-C—Unassisted Thermally Induced Reaction

In accordance with this procedure, the reductive coupling reaction was effected in an nmr tube (5 mm O.D.) to which the solvent, metal compound, non-cyclic oxymethylene source (and acetaldehyde reactant when used) were charged sequentially. The tube was sealed under vacuum and completely wrapped in aluminum foil to exclude light. Temperature was controlled at the desired level by means of an oil bath. Where indicated in the detailed description of the examples, the progress of the reaction was monitored at various intervals by use of nmr spectroscopy. At the end of the reaction period, the reaction mixture was treated in accordance with one or more of the procedures described hereinbelow as Procedures II-A, II-B, II-C, or as otherwise indicaed in the specific description of the examples.

Procedure I-D—Use of Free Radical Initiators

In accordance with this procedure, the reductive coupling reaction was effected in an nmr tube (5 mm O.D.) to which the solvent, metal compound, non-cyclic oxymethylene source (and acetaldehyde reactant when used) and free radical initiator were charged sequentially. The tube was sealed under vacuum and was completely wrapped in aluminum foil to exclude light. Temperature was controlled at the desired level by means of an oil bath. Where incidated in the detailed description of the examples, the progress of the reaction was monitored at various intervals by use of nmr spectroscopy. At the end of the reaction period, the reaction mixture was treated in accordance with one or more of the procedures described hereinbelow as Procedures II-A, II-B, II-C, or as otherwise indicated in the specific description of the examples.

II. Procedures For Treatment Of the Reductively Coupled Reaction Product ("Work-Up")

Procedure II-A—Addition of Acetone + Analysis

In this procedure, acetone was added to the reaction product formed during the reductive coupling reaction and the solution then analyzed by nmr spectroscopy, unless indicated otherwise, to determine the presence of a variety of reaction products.

Procedure II-B—Hydrolysis

In accordance with this procedure, the reaction product formed during the reductive coupling reaction was combined in an nmr tube with 0.48 ml. of water and 1.5 ml. of acetone. After sealing under vacuum, the tube was heated at 150° C. for one hour. Additional acetone (0.30 ml.) was then added, and the mixture filtered to give a precipitate and two liquid phases referred to as the "less dense phase" and the "more dense phase." Unless indicated otherwise, the respective liquid phases where then analyzed by nmr spectroscopy to determine the content of methanol and glycol products. The results of these analyses were then used to calculate the percent conversions to these respective products, based on the amount of oxymethylene reactant charged to the initial reductive coupling reaction. In some examples wherein ethylene glycol, or ethylene glycol plus propylene glycol, was formed the less dense and/or the more dense liquid phases were treated with benzoyl chloride to isolate the glycol(s) as the corresponding dibenzoate derivative(s). These derivatization procedures are described in the context of the particular examples in which they were applied.

Procedure II-C—Hydrostannolysis

In accordance with this procedure, the reaction product of one of the above-described reductive coupling reactions was combined in an nmr tube with a molar amount of dibutyltindihydride, $(C_4H_9)_2SnH_2$, which was five (5) times the molar amount of 1,2-dioxyethylene product which by nmr was found in the reaction mixture. The tube was then sealed under vacuum and heated at 98° C. for one hour. Acetone (1.0 ml.) was added and the supernatant liquid was separated from the mixture of oil and precipitate. The supernatant liquid was then analyzed by nmr spectroscopy to determine the content of alcohol and polyhydric alcohol products. The results of this analysis were then used to calculate the present conversion to these respective products, based on the amount of aldehyde reactant charged to the initial reaction. The supernatant liquid from a number of hydrostannolysis reactions were combined and the combined solutions were treated with benzoyl chloride to form the corresponding dibenzoate derivative of the glycol product. Further details of this derivatization procedure are given in the context of the typical procedure which follows:

A Typical Procedure

The mixture resulting from the addition of 0.370 g (1.58 mmoles) of $Bu_2SuH_2$ to a reaction mixture as empolyed in Example 26, infra (See Table II) was sealed under vacuum in an nmr tube and heated to 98° for 1 hr. Acetone (1.0 ml) was added and the supernatant liquid (0.91 g) separated from the mixture of oil and precipitate. It contained 0.87 mmole of methanol and 0.55 mmole of glycol.

III. General Comments Concerning The Results

A. As noted above, the results are expressed in terms of percent conversion, that is, the percentage of product(s) formed based on the total amount of hydrated or acetalized formaldehyde (expressed as monomeric formaldehyde) charged to the reaction. Inasmuch as the amount of unreacted formaldehyde was not determined, percent yields of product(s) are unknown, that is, the percentage of product(s) formed based on only that amount of formaldehyde which actually reacted. The percent yields would, of course, be at least as high as the percent conversions.

B. The efficiencies of the unoptimized reactions which free glycol from the product(s) of the initial metal compound/aldehyde reaction(s) are unknown but it may be assumed that they are less than 100 percent. Based on this assumption, the amount of glycol produced is less than the amount of formaldehyde that was reductively coupled.

C. As described under general Procedures I-A to I-D hereinabove, the progress of the initial reaction was often monitored by nmr spectroscopy. Because of the insolubility of ethylene glycol in benzene, the use of nmr would not show the presence of any glycol even if it had formed during the reductive coupling reaction. (Whether glycol forms during the initial reaction was determined by other techniques such as above-described Procedure II-A.) However, observation of the nmr spectrum during the course of the reaction does indicate the presence and amount of hydrogen of the type.

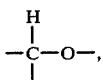

which is in solution. When the progress of the reaction was monitored by nmr spectroscopy, the reaction was stopped when the amount of

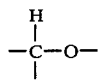

in solution, which increased and then decreased, was near maximum. However, since the product(s) of reductive coupling are not all soluble in the reaction medium, the reaction was not necessarily stopped when the total amount of

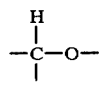

produced was near maximum, due to the possibility that the maximum of the solid portion of the reaction mixture may not have been the same as the maximum of the product in solution.

Above factors A, B and C all make the outcome of the conversion of formaldehyde to ethylene glycol appear less favorable, or at least no more favorable, than it actually is.

Example 1

(A) Photochemical Initiation

Following above-described Procedure I-A, two nmr tubes were charged with approximately equal portions of 15.7 mmoles of benzene, 1.39 mmoles of dibutyltin, and 3.23 mmoles of alpha-polyoxymethylene. The tubes were irradiated with the sunlamp and kept at about 96°–99° C. for 2.7 hours. The progress of the reaction was monitored after 60, 90, 120, 140 and 160 minutes by nmr spectroscopy. Gas chromatorgraphic analysis of the final reaction mixture indicated only a very small amount of methanol and no ethylene glycol.

(B) Hydrolysis

Following above-described general Procedure II-B, the reaction mixture contained in the tubes described under Part A of this example was combined in a tube with the 0.48 ml. of water and 1.5 ml. of acetone. The tube was sealed and heated at 150° C. for one hour. Additional acetone (0.3 ml.) was added as rinse. The resulting mixture was then filtered to give 0.191 gram of precipitate and two liquid phases. By nmr analysis, the less dense phase (1.05 grams) was shown to contain traces of methanol and ethylene glycol. The denser phase (0.42 gram) contained 0.03 mmole of methanol and 1.19 mmoles of ehtylene glycol, based upon nmr analyses. The overall conversion to methanol and ethylene glycol, based on the total amount (3.23 mmoles) of polyoxymethylene charged, are 0.8 mole percent methanol and 37 mole percent ethylene glycol. It is probable that the limiting stoichiometries of the formation of the glycol precursor produced druing the initial reaction, are formaldehyde in amounts of one and two times the molar amount of dibutyltin charged. Taking this probability into account, the percent conversions can be recalculated. Thus, excluding from the total amount of polyoxymethylene charged that amount in excess of two times the amount of tin compound charged (i.e., excluding 0.45 mmole), the percent conversions to methanol and ethylene glycol are 0.9 and 43 mole percent, respectively. For example, the calculation for glycol is as follows:

$$1.2/2.78 \times 100 = 43\%$$

Excluding from the total amount of polyoxymethylene charged that amount in excess of one times the amount of tin compound (i.e., excluding 1.84 mmoles), the percent conversions to methanol and glycol are 1.8 and 86 mole percent, respectively. For example, the calculation of glycol is as follows;

$$1.2/1.39 \times 100 = 86\%$$

(C) Hydrolysis of 1,3,2-Dioxastannolane

This material which has the nominal structure,

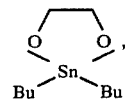

was hydrolyzed following substantially the same hydrolysis procedure described hereinabove as Procedure II-B.

Thus, a mixture of 97 mg. (0.33 mmole) of this material, 1.5 ml. of benzene, 0.6 ml. of water, and 1.9 ml. of acetone was heated in a sealed tube at 150° C. for one hour. Acetone (0.25 ml.) was added and the reaction mixture was filtered to give 77 mg. of precipitate and two liquid phases. The less dense phase (2.57 grams) contained no reaction products (nmr spectrum) and the denser phase (0.76 gram) contained 15.5 mg. (0.25 mmole) of ethylene glycol, corresponding to a 76 percent conversion based on the initial charge of the dioxastannolane.

(D) Derivatization of Glycol From Hydrolyzed Product

1. In order to demonstrate that ethylene glycol can be recovered from aqueous solutions in which the glycol concentration is at about the same level as in the hydrolyzed reaction products of the process of this invention, the following experiment was performed:

To a solution containing 37 mg. (0.60 mmole) of ethylene glycol, 0.61 ml. of water, and 1.65 ml. of 10% NaOH was added 170 μl. of benzoyl chloride. The mixture was stirred vigorously for 10 minutes, then occasionally for 30 minutes, and then held in a 0° C. bath for 1 hour with periodic stirring. Water (1.65 ml.) was then added and the mixture stirred vigorously for one minte, then filtered. The precipitate was washed twice with water (1.65 ml. per wash) and dried to give 60 mg. (37%) of ethylene glycol dibenzoate (m.p.=70.5°–72.5° C.).

2. The 0.76 gram of denser liquid phase described in Part (C) of this example was evaporated, starting at ambient conditions, by slowly lowering the pressure to 100 mm and raising the temperature to 30° C. The residue was treated with 0.26 ml. of water, 0.69 ml. of 10% NaOH, and 71 μl. of benzoyl chloride. The mixture was then treated substantially as described under D(1) above. Thus, the mixture was stirred vigorously for 10 minutes, then occasionally for 30 minutes, and then held in a 0° C. bath for one hour with periodic stirring. Water (0.69 ml.) was then added and the mixture stirred vigorously for one minute, then filtered. The precipitate was washed twice with water (0.69 ml. per wash) and dried to yield 13 mg. (19%) of ethylene glycol dibenzoate (m.p.=70.5°–72.5° C.).

3. Referring now to Part (B) of this example, the 1.05 grams of the less dense liquid phase portion of the hydrolyzed reductively coupled reaction product of Part (A) was worked up following the procedure of Part D(2). Thus, the said liquid phase was evaporated, starting at ambiend conditions, by slowly lowering the pressure to 100 mm and raising the temperature to 30° C. The residue was treated with 0.32 ml. of water, 1.65 ml. of 10% NaOH and 170 μl. of benzoyl chloride. The mixture was then treated substantially as described under D(1) above. Thus, the mixture was stirred vigorously for 10 minutes, then occasionally for 30 minutes, and then held in a 0° C. bath for one hour with periodic stirring. Water (1.65 ml.) was then added. The mixture was stirred vigourously for one minute and then filtered. The solids were rinsed with filtrate, then with water and vacuum dried. Only a trace amount of solids had formed.

4. Referring again to Part (B) of this example, the 0.42 gram of the more dense liquid phase porton of hydrolyzed reductively coupled reaction product of Part (A), was worked up following the procedure applied to the less dense phase as described under Part D(3). Thus, the more dense liquid phase was evaporated, starting at ambient conditions, by slowly lowering the pressure to 100 mm and raising the temperature to 30° C. The residue was treated with 0.31 ml. of water, 1.65 ml. of 10% NaOH and 170 μl of benzoyl chloride. The resulting mixture was stirred vigorously for 10 minutes, then occasionally for 30 minutes, and then held in a 0° C. bath for one hour with periodic stirring. Water (1.65 ml.) was then added and the mixture stirred vigorously for one minute, then filtered. The precipitate was washed twice with water (1.65 ml. per wash) as described under Part D(2) of this example, and dried to yield 30 mg. of ethylene glycol dibenzoate, m.p. 68°–69.5° C.; mixed melting point with authentic material [prepared according to Bornstein, J., et al., Journal of Organic Chemistry, 24, 886 (1959), and Cheronis et al., "Semimicro Qualitative Organic Analysis," Interscience, 1957, p. 383, m.p. 71°–72° C.; nmr $(CDCl_3)$:[tau=1.5–2.7 (m, 10.0H), 5.26(s,3.9H)], 69°–71° C.]

TABLE I

| | | | | Procedure, Supra | | Overall % Conversion[a] to | |
|---|---|---|---|---|---|---|---|
| Example | Solvent, mmoles | $CH_2O$ mmoles | Reaction Conditions | Reaction | Work-up | Methanol | Glycol |
| Control Reactions of α-Polyoxymethylene | | | | | | | |
| 2[a] | Benzene, 6.92 | 1.35 | sunlamp, ~32°/100 hr | I-A | II-B | not determined | 0 |
| 3[b] | Benzene, 5.29 | 0.66 | sunlamp, ~97°/3.5 hr[b] | I-A | II-B | trace | 0 |
| 2[c] | Benzene, 6.57 | 1.23 | sunlamp, ~97°/24 hr | I-A | II-B | 0.6 | 0 |
| 3 | Acetone, 8.72 | 0.92 | sunlamp, ~97°/3 hr | I-A | II-B | trace | trace |
| 4[a] | Benzene, 7.37 | 1.00[e] | 98 °/2 hr[b] | I-C | II-A[c] | not determined | 0 |
| | | | | | II-B | not determined | 0 |
| 4[b] | Benzene, 4.73 | 0.38 | 120°/24 hr | I-C | II-B | 0 | 0 |
| 5 | Benzene, 6.13 | 1.10 | 0.042 mmole AIBN[d], 75°/30 hr | I-D | II-A[c] | 0 | 0 |
| | | | | | II-B | >1.0 | 0 |
| 6[a] | Benzene, 7.58 | 1.00 | 0.38 mmole $(Bu^tO)_2$[d], 130°/30 hr | I-D | II-B | >trace | perhaps trace |
| 6[b] | Benzene, 6.16 | 1.03 | 0.068 mmole $(Bu^tO)_2$[d], 150°/1 hr | I-D | II-B | 1.0 | trace |

[a]See footnote a of Table II infra.
[b]progress of reaction monitored.
[c]0.5 of acetone added.
[d]"AIBN" - azobis (isobutyro) nitrile; "$(Bu^tO)_2$" - di-t-butylperoxide
[e]1.09 mmoles of methanol also present.

EXAMPLES 7–45

In accordance with these examples $(Bu_2Sn)_x$ and α-polyoxmethylene were reacted in either benzene or acetone solvent at various temperatures and reaction times. The reaction products were then either simply homogenized with acetone (Procedure II-A) and analyzed without being reacted further or were treated following Procedure II-B or II-C. The amount of the reactants and solvent, the reaction conditions, variations in procedure, and the results of these examples are given in the Table II which follows.

Derivatization of Glycol From Hydrolyzed Product

1. Referring again to the typical procedure provided under procedure II C above, the 0.91 g of supernatant liquid was combined with the solutions obtained similarly from examples 21 and 24. The resulting solution was evaporated at ~30°/100 mm to yield a viscous residue to which was added 0.31 ml of water and 1.65 ml of 10% NaOH. The resulting mixture was filtered. To the filtrate was added 0.170 μl of benzoyl chloride and the mixture treated as described in D1 to yield 25 mg of precipitate, mp 64°–8°, which contained a very small amount of refractory material. The precipitate was extracted with 0.45 ml of $CDCl_3$. Evaporation of the extract yielded 18 mg of product, mp 63°–70°, whose nmr spectrum indicated only absorptions attributable to ethylene glycol dibenzoate.

2. The denser phase (0.92 g, containing 0.70 mmole of glycol) from the work-up of example 44 was treated as described in D3 above to yield 18 mg of product whose nmr spectrum indicated only absorptions attributable to ethylene glycol dibenzoate. Similarly, the less dense phase (5.12 g, containing 0.52 mmole of glycol) yielded 7 mg of such product.

3. The solution from the hydrolysis of example 28 was treated as described in D3 above to give product whose nmr spectrum indicated only absorptions attributable to ethylene glycol dibenzoate.

zene solvent at various temperatures and reaction times. The reaction products were then treated following procedure II-B. The amount of the reactants and solvent, the reaction conditions, variations, in procedure,

TABLE II

Reaction of $(Bu_2Sn)_x$ (dibutyltin) and α-Polyoxymethylene

| Example | Solvent, mmoles | Reactants, mmoles | | Reaction Conditions | Procedure | | Overall % Conversion[a] to | |
|---|---|---|---|---|---|---|---|---|
| | | $(Bu_2Sn)$ | $CH_2O$ | | Reaction | Work-up | Methanol | Glycol |
| 7 | Benzene, | 4.82 | 0.36 | 1.19 | sunlamp, ~ 34°/3 hr | I-A | II-A[d] | 0 | 0 |
| | | | | | | | II-B | 0.3(0.5–1.0) | 0.8(1.3–2.6) |
| 8 | | 4.82 | 0.30 | 1.15 | sunlamp, ~ 34°/24 hr | I-A | II-A[d] | trace | very small |
| 9 | | 4.19 | 0.32 | 1.22 | sunlamp, ~ 34°/24 hr | I-A | II-B | 1.5 | ≧8(≧15–≧30) |
| 10 | | 3.45 | 0.23 | 0.55 | sunlamp, ~ 34°/89 hr[b] | I-A | II-B | 1.3(1.6–3.2) | 33(39–78) |
| 11[j] | | 4.81 | 0.34 | 1.25 | sunlamp, ~ 34°/100 hr | I-A | II-B | 4(7–14) | 31(57–114) |
| 12 | | 4.13 | 0.41 | 0.62 | sunlamp, ~ 75°/2.8 hr[b] | I-A | II-B | trace | ~29(29–44) |
| 13 | | 12.7 | 0.12 | 2.12 | sunlamp, ~ 98°/2.5 hr[b] | I-A | II-B | 5.4(48–96) | ≧5.3(≧47–≧94) |
| 14 | | 5.30 | 0.132 | 0.97 | sunlamp, ~ 98°/3 hr[b] | " | II-B | ≧1.8(≧6.6–≧12) | 24(88–176) |
| 15 | | 4.92 | 0.32 | 1.20 | sunlamp, ~ 98°/2.5 hr[b] | " | II-A[d] | not determined | very small |
| 16 | | 4.37 | 0.44 | 0.71 | sunlamp, ~ 98°/2 hr[b] | " | II-B | trace | 11(11–18) |
| 17 | | 4.28 | 0.43 | 0.70 | sunlamp, ~ 98°/2.5 hr[b] | " | II-B | 0 | 19(19–31) |
| 18 | | 4.79 | 0.49 | 1.08 | sunlamp, ~ 98°/2.8 hr[b] | " | II-B | trace | 28(31–62) |
| 19 | | 4.77 | 0.42 | 1.40 | sunlamp, ~ 98°/4 hr[b] | " | II-B | ≧1.2(≧2–≧4) | 35(60–120) |
| 20 | | 4.72 | 0.42 | 1.40 | sunlamp, ~ 98°/3 hr[b] | " | II-B | 0.6(1–2) | 25(42–83) |
| 21 | | 4.48 | 0.48 | 1.27 | sunlamp, ~ 98°/3 hr[b] | " | II-C | 20(26–52)[e] | 15(20–40) |
| 22[g] | | 5.36 | 0.47 | 1.12 | sunlamp, ~ 98°/24 hr | " | II-B | at most very little | 38(45–90) |
| 23 | | 3.86 | 0.76 | 1.34 | sunlamp, ~ 98°/2.5 hr[b] | " | II-C | 10.4(10.4–18)[e] | 9.7(9.7–17) |
| 24 | | 7.87 | 0.68 | 2.11 | sunlamp, ~ 95°/3.5 hr[b] | " | II-C | 11(17–34)[e] | 16(25–50) |
| 25 | | 7.25 | 0.68 | 2.13 | sunlamp, ~ 95°/3.5 hr[b] | " | II-C | 41(64–128)[e] | 26(41–82) |
| 26 | | 15.7 | 1.39 | 3.23 | sunlamp, ~ 98°/2.7 hr[b] | " | II-B | 0.8(0.9–1.8) | 37(43–86) |
| 27 | Acetone | 8.82 | 0.43 | 0.92 | sunlamp, ~ 95°/3 hr | " | II-B | 2.5(2.7–5.4) | 34(36–72) |
| 28 | | 13.4 | 0.62 | 1.54 | sunlamp, ~ 98°/3 hr | " | II-B | 0.9(1.1–2.2) | 31(39–78) |
| 29[c] | Benzene | 6.02 | 0.69 | 1.29 | 98°/1hr, 130°/1 hr; sunlamp, ~ 98°/6hr[b] | I-C; I-A | II-B | 9 | 18(18–34) |
| 30 | | 4.20 | 0.16 | 0.64 | 450w medium pressure Hg lamp, ~ 31°/1hr, ~ 80°/2hr[b] | I-B | II-B | 1.6(3.2–6.4) | >5(>10–>20) |
| 31 | | 4.56 | 0.36 | 0.55 | 450w medium pressure Hg lamp, ~ 80°/3hr[b] | I-B | II-B | trace | 23(23–35) |
| 32 | Benzene | 4.29 | 0.36 | 1.05 | 80°/5 hr | I-C | II-B | ≧2.0(≧2.9–≧5.8) | 3.1(4.5–9) |
| 33 | Benzene, | 4.32 | 0.33 | 1.13 | 80°/24 hr | " | II-A[d] | not determined | 0 |
| | | | | | | | II-B | 4.6(7.9–16) | ≧3.0(≧5.1≧10) |
| 34 | | 5.01 | 0.40 | 1.21 | 98°/2 hr | " | II-B | 1.2(1.8–3.6) | 1.9(2.9–5.8) |
| 35 | | 4.56 | 0.39 | 1.25 | 98°/5 hr | " | II-A[d] | not determined | 0 |
| | | | | | | | II-B | 4.8(7.7–15) | ≧0.6(1.0–2) |
| 36 | | 4.53 | 0.37 | 1.23 | 130°/2 hr | " | II-B | 7.8(13–26) | trace |
| 37 | | 6.62 | 0.56 | 1.28 | 150°/hr[b] | " | II-B | 0.6(0.7–1.4) | 0 |
| 38 | | 4.88 | 0.41 | 0.95 | 0.17 mmole AlBN, 75°/30 hr | I-D | II-A[d] | not determined | 0 |
| | | | | | | | II-B | 6.6 (7.6–15) | trace |
| 39[g] | | 5.68 | 0.39 | 1.02 | 0.039 mmole AlBN, 75°/30 hr[b] | " | II-A[d] | not determined | 0 |
| | | | | | | | II-B | 8(10–20) | 3.8(5–10) |
| 40 | | 4.43 | 0.39 | 1.24 | 0.046 mmole AlBN, 40°/1 hr | " | II-A[d] | 0 | 0 |
| | | | | | | | II-B | 4.3(6.9–14) | trace |
| 41 | | 4.61 | 0.45 | 1.11 | 0.044 mmole $Bz_2O_2$, 98°/7 hr[b] | " | II-A[d] | not determined | 0 |
| | | | | | | | II-B | >4.3(5.3–10.6) | trace |
| 42[h] | | 5.44 | 0.53 | 1.19 | 0.36 mmole $(Bu^tO)_2$, 130°/30 hr | " | II-B | ≧1.8(≧2.0–≧4.0) | 7.9(8.9–18) |
| 43 | | 5.85 | 0.36 | 1.12 | 0.075 mmole $(Bu^tO)_2$, 130°/30 hr[b] | " | II-B | 3.2(5–10) | ≧6.9(11–22) |
| 44 | | 31.2 | 3.01 | 6.59 | 2.0 mmoles $(Bu^tO)_2$, 150°/1 hr | " | II-B | ≧1.0(≧1.1–≧2.2) | 18(20–40) |
| 45[i] | | 4.88 | 0.55 | 1.02 | 0.068 mmole $(Bu^tO)_2$, 150°/1 hr | " | II-B | ≧2.4(≧2.4–≧4.5) | 13(13–24) |

[a] By nmr analysis, unless indicated otherwise (Qualitative confirmations made by use of vpc are not indicated) Based on starting formaldehyde. (Numbers in parentheses result from exclusion from the calculation of any formaldehyde in excess of 1-2X the molal amount of $(Bu_2Sn)$; these probably represent the limiting stoichiometries of formation of pro-glycol)
[b] Reaction progress followed.
[c] Prior heating appears to transform $(Bu_2Sn)_x$ into a less effective catalyst of the photochemically-initiated reaction.
[d] 0.5 ml of acetone added.
[e] Work-up II-C would convert unreacted formaldehyde to methanol (See Table VI).
[f] cf. example 2c in Table I.
[g] cf. example 5 in Table I.
[h] cf. example 6a in Table I.
[i] cf. example 6b in Table I.
[j] cf. example 2a in Table I.

EXAMPLES 46-67

In accordance with these examples, several tin compounds and α-polyoxymethylene were reacted in benzene and the results of these examples are given in the Table III which follows.

TABLE III.

Reaction of Miscellaneous Tin Compounds and α-Polyoxymethylene

| Example | Solvent, mmoles | Reactants, mmoles Tin Compound | | CH₂O | Reaction Conditions | Procedure[e] Reaction | Overall % Conversion[c] to Methanol | Glycol |
|---|---|---|---|---|---|---|---|---|
| 46 | Benzene, 5.23 | Bu₂Sn(OAc)₂, | 0.49 | 1.13 | sunlamp, 98°/20 hr[d] | I-A | 0.4(1.0)[b] | 1.4(3.2)[b] |
| 47 | Benzene, 5.04 | Bu₂SnO,[a] | 0.48 | 1.14 | sunlamp, 93-8°/5 hr[d] | I-A | trace | 0 |
| 48 | Benzene, 5.39 | SnCl₂, | 0.50 | 1.16 | sunlamp, 93-8°/8 hr[d] | I-A | trace | 0 |
| 49 | Benzene, 5.12 | Sn(OAc)₂, | 0.54 | 1.14 | sunlamp, 93-8°/2.5 hr[d] | I-A | trace | 0 |
| 50 | Benzene, 5.31 | SnO, | 0.55 | 1.18 | sunlamp, 98°/20 hr[d] | I-A | trace | 0 |
| 51 | Benzene, 5.28 | SnF₂, | 0.47 | 1.06 | sunlamp, 98°/20 hr[d] | I-A | trace | 0 |
| 52 | Benzene, 5.77 | (PhCO₂Ph₂Sn)₂[a] | 0.34 | 0.72 | 140°/1.5 hr[d] | I-C | 15(16-32)[b] | 0 |
| 53 | Benzene, 5.94 | " | 0.30 | 0.67 | sunlamp, ~98°/13 hr[d] | I-A | 2.7(3-6)[b] | 8(9-18)[b] |
| 54 | Benzene, 5.37 | (PhCO₂Bu₂Sn)₂, | 0.29 | 0.77 | 140°/6.5 hr[d] | I-C | 5.3(7.1-14)[b] | 0 |
| 55 | Benzene, 10.4 | " | 0.56 | 1.13 | 120°/53 hr[d] | I-C | 3.4(3.4-6.8)[b] | 0 |
| 56 | Benzene, 6.38 | " | 0.30 | 0.70 | sunlamp, ~98°/5 hr[d] | I-A | 1.6(2-4)[b] | 9(11-22)[b] |
| 57 | Benzene, 11.8 | (AcOPh₂Sn)₂[a], | 0.60 | 1.16 | 120°/3 hr[d] | I-C | 7.0(7.0-13)[b] | trace |
| 58 | Benzene, 5.33 | " | 0.31 | 0.63 | 140°/30 min | I-C | 13(13-26) | trace |
| 59 | Benzene, 5.26 | " | 0.33 | 0.85 | sunlamp, ~98°/16 hr[d] | I-A | 2.5(3.2-6.4)[b] | 7(9-17)[b] |
| 60 | Benzene, 5.73 | Ph₃SnI, | 0.51 | 1.13 | 0.055 mmole(Bu$^t$O)₂, 130°/1 hr | I-D | ≧3.4(≧3.8-≧7.5)[b] | no more than small amount |
| 61 | Benzene, 6.37 | " | 0.53 | 1.11 | sunlamp, ~95°/28 hr[d] | I-A | 6.5(6.8-14)[b] | 0.14(0.15-0.2)[b] |
| 62 | Benzene, 6.42 | Bu₄Sn, | 0.60 | 1.17 | 130°/1 hr | I-C | 0.9(0.9-1.8)[b] | 0.9(0.9-1.8)[b] |
| 63 | Benzene, 6.37 | " | 0.54 | 1.15 | sunlamp, ~98°/9 hr[d] | I-A | ≧1.7(1.8-3.6)[b] | 7(7-15)[b] |
| 64 | Benzene, 6.70 | Me₃SnSnMe₃, | 0.67 | 1.31 | 0.068 mmole (Bu$^t$O)₂, 130°/1 hr | I-D | 5.7(5.7-11)[b] | 14(14-27)[b] |
| 65 | Benzene, 5.64 | " | 0.47 | 1.13 | sunlamp, ~98°/7 hr[d] | I-A | trace | 46(55-111)[b] |
| 66 | Benzene, 6.22 | Sn(325 mesh), | 0.48 | 1.07 | 0.068 (Bu$^t$O)₂, 130°/1 hr | I-D | ~1(~1 to ~2)[b] | trace |
| 67 | Benzene, 6.13 | " | 0.49 | 0.97 | sunlamp, ~98°/4 hr[d] | I-A | 2(2-4) | 0 |

[a]Insoluble in benzene
[b]Numbers in parentheses result from excluding from the calculation any formaldehyde in excess of the molal amount of tin compound; this probably represents the limiting stochiometry of formation of pro-glycol
[c]See footnote (a) of Table II supra.
[d]See footnote (b) of Table I supra.
[e]Work-up all II-BB

EXAMPLES 68–76

In accordance with these examples (AcOBu₂Sn)₂ and (Bu₂Sn)x were reacted with α-polyoxymethylene in benzene solvent at various temperatures and reaction times in the presence of methanol. Since methanol and formaldehyde are known to react under free radical conditions to give ethylene glycol [M. Oyama, J. Org. Chem., 30, 2429 (1965)], the following questions were addressed: Might methanol be an intermediate in the conversion of formaldehyde to pro-glycol in the present reaction? Can methanol be converted to pro-glycol under the reaction conditions? The reaction products were either simply homogenized with acetone (Procedure II-A) and analyzed without being reacted further or were hydrolyzed following procedure II-B. The amount of reactants and solvent, the reaction conditions, variations in procedure, and the results of these examples are given in the Table IV which follows. There is no evidence for the involvement of methanol in the production of pro-glycol. It may, however, indirectly increase the rate by solubilizing the α polyoxymethylene.

TABLE IV.

Reaction of Tin Compounds and α-Polyoxymethylene. Effect of Methanol

| Example | Solvent, mmoles | Reagents, mmoles Tin Compound | | CH₂O | MeOH | Reaction Conditions | Procedure Reaction | Work-up | Overall % Conversion[c] to Methanol | Glycol |
|---|---|---|---|---|---|---|---|---|---|---|
| 68 | Benzene, | 5.67 | (AcOBu₂Sn)₂, 0.49 | 1.08 | 2.21 | sunlamp, ~98°/9 hr | I-A | II-B | j | 29(32-64) |
| 69 | | 7.37 | — | 1.00 | 1.09 | 98°/2 hr[d] | I-C | II-A[a] II-B | | 0 |
| 70 | | 5.11 | Bu₂Sn, 0.44 | 1.12 | 1.02 | 98°/2 hr[d] | " | II-A[a] | | 0 |
| 71 | | 4.87 | 0.40 | 1.00 | 0.98 | 98°/2 hr[d] | " | II-B | h | 4(5-10) |
| 72 | | 4.78 | 0.32 | — | 0.91 | 98°/4 hr[d] | " | II-A[a] II-B | f | 0 0 |
| 73 | | 4.86 | 0.29 | — | 0.98 | sunlamp, ~98°/28 hr[d] | I-A | II-A[a] II-B | g | 0 0 |
| 74(m) | | 4.63 | 0.38 | 1.20 | 1.05 | sunlamp, ~98°/3 hr | " | II-B | i | 37(59-113) |
| 75(m) | | 4.44 | 0.41 | 1.17 | 1.00 | sunlamp, ~98°/3 hr[d] | " | II-B | f | 46(61-122)[l] |
| 76(m) | | 4.72 | 0.46 | 1.13 | 1.12 | sunlamp, ~98°/3 hr[d] | " | II-B | f | 39(48-96) |

[a]0.5 ml of acetone added
[c]See footnote a of Table II. Read Bu₂Sn or (AcOBu₂Sn)₂ as appropriate
[d]Progress of reaction monitored.
[f]81% of reactant methanol
[g]105% of reactant methanol
[h]82% of reactant methanol
[i]31% of reactant methanol
[j]89% of reactant methanol
[l]Analysis less accurate than usual.
[m]Compare to examples 19 and 20 in Table II, which had about the same starting Bu₂Sn/CH₂O ratio.

EXAMPLES 77–91

In accordance with these examples AcOBu₂SnSnBu₂OAc and α-polyoxymethylene were reacted in benzene solvent at various temperatures and reaction times.

The reaction products were then either simply homogenized with acetone (Procedure II-A) and analyzed without being reacted further or were treated following Procedure II-B. The amount of the reactants and solvent, the reaction conditions, variations in procedure, and the results of these examples are given in the Table VI which follows.

TABLE VI.

Reaction of $Bu_2SnH_2$ and $\alpha$-Polyoxymethylene

| Example | Solvent, mmoles | Reactants, mmoles $Bu_2SnH_2$ | $CH_2O$ | Reaction Conditions | Procedure Reaction | Work-up | % Conversion[a] to Methanol | Glycol |
|---|---|---|---|---|---|---|---|---|
| 92 | Benzene, 7.72 | 0.82 | 1.64 | sunlamp, ~ 98°/2 hr[d] | I-A | II-A[b] | not determined[c] | 0 |
| 93 | 6.28 | 0.63 | 1.33 | room temp./2 hr, then ~ 92°/2 hr[d] with sunlamp | I-C; I-A | — | no reaction | |
|  |  |  |  |  |  | — | 32(34–68) | not determined |
|  |  |  |  |  |  | II-B | 35(37–74) | 14(15–30) |
| 94 | 11.8 | 0.59 | 1.11 | room temp./31 hr[d] | I-C | II-A[b] | not determined[c] | 0 |
|  |  |  |  |  |  | II-B | 23(23–43) | 0 |
| 95 | 11.5 | 0.80 | 1.12 | 0.038 mmole AIBN, room temp./5 hr[d] | I-D | II-B | 38(38–53) | 0 |

[a]See footnote a of Table II; for $Bu_2Sn$, read $Bu_2SnH_2$.
[b]0.5 ml of acetone added
[c]A substantial amount was present.
[d]Progress of reaction monitored.

vent, the reaction conditions, variations in procedure, and the results of these examples are given in the Table V which follows.

Derivatizations of Glycol from Hydrolyzed Product

The denser phase (0.43 g, containing 0.40 mmole of glycol) from the work-up of example 80 was treated as described in D3 above to yield 9 mg. of ethylene glycol dibenzoate, mp 64°–70°, mixed mp with authentic material 67°–71°, whose nmr spectrum ($CDCl_3$) agreed with that of authentic material.

EXAMPLES 96–103

In accordance with these examples $Bu_3SnSnBu_3$ and $\alpha$-polyoxymethylene were reacted in benzene solvent at various temperatures and reaction times. The reaction products were then hydrolyzed following Procedure II-B. The amount of the reactants and solvent, the reaction conditions, variations in procedure, and the results of these examples are given in the Table VII which follows.

TABLE V

Reaction of $AcOBu_2SnSnBu_2OAc$ and $\alpha$-Polyoxymethylene

| Example | Solvent, mmoles | Reactants, mmoles $(AcOBu_2Sn)_2$ | $CH_2O$ | Reaction Conditions | Procedure Reaction | Work-up | Overall % Conversion[b] to Methanol | Glycol |
|---|---|---|---|---|---|---|---|---|
| 77 | Benzene, 5.64 | 0.22 | 1.37 | sunlamp, ~ 98°/4 hr | I-A | II-B | 5.2(16–32) | 16(50–100) |
| 78 | 5.33 | 0.51 | 1.18 | sunlamp, ~ 97°/3 hr | I-A | II-A[a] | 0 | not determined |
|  |  |  |  |  |  | II-B | 4.2(4.9–10) | ≧11(≧13–≧26) |
| 79 | 5.18 | 0.53 | 1.19 | sunlamp, ~ 98°/9 hr[d] | I-A | II-B | 5(5.6–11) | 26(29–58) |
| 80 | 13.7 | 1.63 | 3.52 | sunlamp, ~ 98°/9 hr | I-A | II-B | 3.4(3.7–7.4) | 15(16–32) |
| 81 | 5.36 | 0.56 | 1.23 | sunlamp, ~ 97°/24 hr | I-A | II-B | 5(5–11) | 27(30–60) |
| 82 | 5.63 | 0.52 | 1.27 | 98°/28 hr[d] | I-C | II-B | 25(31–62) | trace |
| 83 | 5.00 | 0.29 | 0.42 | 110°/30 hr[d] | I-C | none | 12(29–51) | not determined |
| 84 | 5.67 | 0.35 | 0.37 | 120°/24 hr | I-C | none | 0 | 0 |
| 85 | 5.74 | 0.24 | 0.86 | 130°/2.5 hr[d] | I-C | II-B | 7(13–26) | 0 |
| 86 | 5.38 | 0.54 | 0.71 | 130°/3 hr[d] | I-C | II-B | 51(51–67) | 0 |
| 87 | 5.15 | 0.25 | 0.70 | 130°/2.5 hr[d] | I-C | II-B | 24(34–68) | not determined |
| 88 | 4.70 | 0.28 | 0.49 | 130°/2.5 hr[d] | I-C | II-B[c] | 29(29–51) | not determined |
| 89 | 34.5 | 1.94 | 3.94 | 130°/2.8 hr[d] | I-C | II-B | 38(39–78)[e] | 0 |
| 90 | 5.38 | 0.34 | 0.70 | 140°/50 min[d] | I-C | II-B | 19(20–40) | 0 |
| 91 | 5.77 | 0.44 | 1.06 | 0.043 mmole AIBN, 90°/1 hr | I-D | II-A[a] | 0 | 0 |
|  |  |  |  |  |  | II-B | 11(13–26) | trace |

[a]0.5 ml of acetone added.
[b]See footnote a of Table II; for $Bu_2Sn$ read $(AcOBu_2Sn)_2$
[c]A possibly inferior variant of the usual procedure was used.
[d]Progress of reaction monitored.
[e]Determined also by use of vpc analysis.

EXAMPLES 92–95

In accordance with these examples $Bu_2SnH_2$ and $\alpha$-polyoxymethylene were reacted in benzene solvent at various temperatures and reaction times. The reaction products were then either simply homogenized with acetone (Procedure II-A) and analyzed without being reacted further or were treated following Procedure Derivatization of Glycol from Hydrolyzed Product The denser phase (0.65 g, containing 1.45 mmoles of glycol) from the work-up of example 97 was treated as described in D3 above to yield 36 mg of ethylene glycol dibenzoate, mp 64°–71°, whose nmr spectrum indicated only absorptions attributable to ethylene glycol dibenzoate.

TABLE VII.

Reaction of $Bu_3SnSnBu_3$ and $\alpha$-Polyoxymethylene

| Example | Solvent, mmoles | Reactants, mmoles $Bu_3SnBu_3$ | $CH_2O$ | Reaction Conditions | Procedure[c] Reaction | Overall % Conversion[a] to Methanol | Glycol |
|---|---|---|---|---|---|---|---|
| 96 | Benzene, 6.62 | 0.52 | 1.20 | sunlamp, ~ 98°/8.5 hr[b] | I-A | 5.5(6.4–13) | 27(31–62) |

TABLE VII.-continued

Reaction of Bu₃SnSnBu₃ and α-Polyoxymethylene

| Example | Solvent, mmoles | Reactants, mmoles Bu₃SnBu₃ | CH₂O | Reaction Conditions | Procedure[c] Reaction | Overall % Conversion[a] to Methanol | Glycol |
|---|---|---|---|---|---|---|---|
| 97 | 24.8 | 2.01 | 4.36 | sunlamp, ~98°/6–22 hr [b] | I-A | ≧0.06(≧0.7-≧1.3) | 44(48–96) |
| 98 | 5.81 | 0.50 | 1.21 | 98°/2 hr | I-C | ≧2.5(≧3.1-≧6) | trace |
| 99 | 6.15 | 0.46 | 1.08 | 130°/2 hr | I-C | 1.1(1.2–2.5) | 0 |
| 100 | 5.91 | 0.52 | 1.00 | 130°/5 hr | I-C | 1.2(1.2–2.3) | 0 |
| 101 | 5.46 | 0.49 | 1.11 | 0.061 mmole AlBN, 90°/1 hr | I-D | >3.3(>3.7–7.4) | trace |
| 102 | 5.74 | 0.50 | 1.03 | 0.052 mmole Bz₂O₂, 98°/1 hr | I-D | >1.8(>1.8->3.6) | trace |
| 103 | 5.82 | 0.48 | 0.99 | 0.068 mmole (Buᵗ O)₂,130°/1 hr | I-D | >0.6(>0.6->1.2) | 5.6(5.8–12) |

[a]See footnote a of Table II; for Bu₂Sn, read Bu₃SnSnBu₃
[b]Progress of reaction monitored.
[c]Work-up all II-B.

EXAMPLES 104–111

In accordance with these examples Ph₃SnSnPh₃ and α-polyoxymethylene were reacted in benzene solvent at various temperatures and reaction times. The reaction products were then hydrolyzed following Procedure II-B. The amount of the reactants and solvent, the reaction conditions, variations in procedure, and the results of these examples are given in the Table VIII which follows.

EXAMPLES 112–118

In accordance with these examples Ph₃SnH and α-polyoxymethylene were reacted in benzene solvent at various temperatures and reaction times. The reaction products were then hydrolyzed following Procedure II-B. The amount of the reactants and solvent, the reaction conditions, variations in procedure, and the results of these examples are given in the Table IX which follows.

TABLE IX.

Reaction of Ph₃SnH and α-Polyoxymethylene

| Example | Solvent, mmoles | Reactants, mmoles Ph₃SnH | CH₂O | Reaction Conditions | Procedure[b] Reaction | Overall % Conversion[a] to Methanol | Glycol |
|---|---|---|---|---|---|---|---|
| 112 | Benzene, 5.08 | 0.52 | 1.15 | sunlamp, ~ 98°/3 hr[c] | I-A | 26(29–58) | 18(20–40) |
| 113 | 7.08 | 0.73 | 1.51 | 98°/2 hr | I-C | 19(20–40) | 0 |
| 114 | 5.23 | 0.61 | 1.53 | 98°/5 hr | I-C | >8(>10->20) | trace |
| 115 | 5.90 | 0.57 | 1.20 | 130°/2 hr | I-C | 15(16–32) | 0 |
| 116 | 4.91 | 0.45 | 1.20 | 0.043 mmole AlBN, 90°/1 hr | I-D | 17(23–46) | 3.0(4–8) |
| 117 | 5.22 | 0.49 | 1.01 | 0.12 mmole Bz₂O₂, 98°/1 hr | I-D | 16(16–32) | 0 |
| 118 | 4.92 | 0.54 | 1.13 | 0.068 mmole (Buᵗ O)₂, 98°/1 hr | I-D | 23(24–48) | 3.9(4–8) |

[a]See footnote a of Table II; for Bu₂Sn, read Ph₃SnH
[b]Work-up all II-B
[c]Progress of reaction monitored

Derivatization of Glycol from Hydrolyzed Product

The denser phase (0.500 g, containing 0.41 mmole of glycol) from the work-up of example 105 was treated as described in D3 above to yield 20 mg of ethylene glycol dibenzoate, mp 63°–8°, mixed mp with authentic material 68°–71°, whose nmr spectrum indicated only absorptions attibutable to ethylene glycol dibenzoate.

The less dense phase (4.88 g, containing 0.42 mmole of glycol) from the work-up of example 105 was treated as described in D3 above to yield 5 mg of material, mp 61°–6°, whose nmr spectrum indicated only absorptions attributable to ethylene glycol dibenzoate.

EXAMPLES 119–126

In accordance with these examples Bu₃SnH and α-polyoxymethylene were reacted in benzene solvent at various temperatures and reaction times. The reaction products were then hydrolyzed following Procedure II-B. The amount of the reactants and solvent, the reaction conditions, variations in procedure, and the results of these examples are given in the Table X which follows.

Derivatization of Glycol from Hydrolyzed Product

The dense phase (1.32 g, containing 1.04 mmoles of glycol) from the work-up of Example 126 was treated as

TABLE VIII.

Reaction of Ph₃SnSnPh₃ and α-Polyoxymethylene

| Example | Solvent, mmoles | Reactants, mmoles Ph₃SnSnPh₃[b] | CH₂O | Reaction Conditions | Procedure[c] Reaction | Overall % Conversion[a] to Methanol | Glycol |
|---|---|---|---|---|---|---|---|
| 104 | Benzene, 6.32 | 0.49 | 1.07 | sunlamp, ~ 98°/24 hr | I-A | ~6(~7-~13) | 20(22–44) |
| 105 | 28.5 | 2.40 | 5.46 | sunlamp, ~ 95°/24 hr | I-A | 4.7(5.4–11) | 15(17–34) |
| 106 | 5.89 | 0.47 | 1.08 | 98°/2 hr | I-C | 1.5(1.7–3.4) | 0 |
| 107 | 6.21 | 0.49 | 1.23 | 130°/2 hr | I-C | trace | 0 |
| 108 | 6.16 | 0.49 | 1.13 | 130°/5 hr | I-C | >trace | 0 |
| 109 | 6.23 | 0.48 | 1.15 | 0.061 mmole AlBN, 90°/1 hr | I-D | 5.9(7.1–14) | 0 |
| 110 | 5.58 | 0.49 | 0.87 | 0.060 mmole Bz₂O₂,98°/1 hr | I-D | 0 | 0 |
| 111 | 5.97 | 0.48 | 1.20 | 0.068 mmole (Buᵗ O)₂,130°/1 hr | I-D | >1.1(>1.4–2.8) | 1.0(1.3–2.5) |

[a]See footnote a of Table II; for Bu₂Sn, read Ph₃SnSnPh₃
[b]Insoluble in benzene
[c]Work-up all II-B described in D3 above to yield 12 mg of product whose nmr spectrum indicated only absorptions attributable to ethylene glycol dibenzoate.

TABLE XI.

Reaction of Ph₃GeH and α-Polyoxymethylene

| Example | Solvent, mmoles | Reactants, mmoles Bu₃SnH | CH₂O | Reaction Conditions | Procedure[c] Reaction | Overall % Conversion[a] to Methanol | Glycol |
|---|---|---|---|---|---|---|---|
| 127 | Benzene, 5.83 | 0.44 | 0.93 | sunlamp, ~ 98°/21 hr[b] | I-A | >10(>11->21) | 2.1(2.2–4.4) |
| 128 | 5.56 | 0.52 | 1.10 | 0.083 mmole (Bu$^t$O)₂, 130°/1 hr | I-D | 31(33–66) | 7(7.4–15) |
| 129 | 6.32 | 0.76 | 1.13 | 0.089 mmole (Bu$^t$O)₂, 130°/1 hr | I-D | 42(42–63) | 10.6(10.6–16) |
| 130 | 6.23 | 0.50 | 1.00 | 0.052 mmole (Bu$^t$O)₂, 130°/3 hr | I-D | 27(27–54) | 12.6(12.6–25) |
| 131 | 24.7 | 2.03 | 4.37 | 0.24 mmole (Bu$^t$O)₂, 130°/3 hr | I-D | >>9(>>10->>20) | 5.7(6.1–12) |

[a]See footnote a of Table II; for Bu₂Sn, read Ph₃GeH
[b]Progress of reaction monitored
[c]Work-up all II-B ethylene glycol dibenzoate.

TABLE X.

Reaction of Bu₃SnH and α-Polyoxymethylene

| Example | Solvent, mmoles | Reactants, mmoles Bu₃SnH | CH₂O | Reaction Conditions | Procedure[c] Reaction | Overall % Conversion[a] to Methanol | Glycol |
|---|---|---|---|---|---|---|---|
| 119 | Benzene, 5.13 | 0.49 | 1.09 | sunlamp, ~ 97°/2 hr[b] | I-A | 17(19–38) | 32(36–71) |
| 120 | 5.52 | 0.43 | 1.11 | 98°/2 hr | I-C | >6(>8->16) | 2.5(3.2–6.5) |
| 121 | 5.19 | 0.50 | 0.95 | 98°/5 hr | I-C | >9(>9->17) | 4.4(4.4–8.4) |
| 122 | 6.74 | 0.48 | 1.17 | 130°/2 hr | I-C | 27(33–66) | 4.0(5–10) |
| 123 | 5.62 | 0.49 | 1.01 | 0.039 mmole AlBn, 90°/1 hr | I-D | >4(>4->8) | 2.7(2.7–5.4) |
| 124 | 5.49 | 0.48 | 1.20 | 0.043 mmole Bz₂O₂, 98°/1 hr | I-D | 22(28–55) | trace |
| 125 | 5.31 | 0.46 | 1.07 | 0.064 mmole (Bu$^t$O)₂, 130°/1 hr | I-D | >4(>5->10) | 16(19–37) |
| 126 | 33.6 | 3.05 | 6.79 | 0.42 mmole (Bu$^t$O)₂, 130°1 hr | I-D | 23(26–51) | 19(21–42) |

[a]See footnote a of Table II; for Bu₂Sn, read Bu₃SnH
[b]Progress of reaction monitored
[c]Work-up all II-B

EXAMPLES 127–131

In accordance with these examples Ph₃GeH and α-polyoxymethylene were reacted in benzene solvent at various temperatures and reaction times. The reaction products were then hydrolyzed following Procedure II-B. The amount of the reactants and solvent, the reaction conditions, variations in procedure, and the results of these examples are given in the Table XI which follows.

EXAMPLES 132–140

In accordance with these examples several germanium compounds and α-polyoxymethylene were reacted in benzene solvent at various temperatures and reaction times. The reaction products were then hydrolyzed following Procedure II-B. The amount of the reactants and solvent, the reaction conditions, variations in procedure, and the results of these examples are given in the Table XII which follows.

TABLE XII.

Reaction of Miscellaneous Germanium Compounds and α-Polyoxymethylene

| Ex. | Solvent, mmoles | Reactants, mmoles Germanium Compound | | CH₂O | Reaction Conditions | Procedure[b] Reaction | Overall % Conversion[a] to Methanol | Glycol |
|---|---|---|---|---|---|---|---|---|
| 132 | Benzene, 6.12 | 352 mesh Ge, | 0.44 | 1.01 | 0.068 mmole (Bu$^t$O)₂, 130°/1 hr | I-D | no more than a very small amount | trace |
| 133 | 6.05 | | 0.49 | 1.17 | sunlamp, ~ 95°/4 hr[d] | I-A | trace | 0 |
| 134 | 6.01 | Bu₄Ge, | 0.48 | 1.03 | 0.048 mmole (Bu$^t$O)₂, 130°/1 hr | I-D | 1.5(1.6–3.2) | 5.9(6.3–13) |
| 135 | 6.43 | | 0.52 | 1.13 | sunlamp, ~ 95°/4 hr[d] | I-A | 1(1–2) | <1(<1–<2) |
| 136 | 6.12 | GeO₂, | 0.50 | 1.00 | 0.015 mmole (Bu$^t$O)₂, 130°/1 hr | I-D | trace | trace |
| 137 | 6.04 | | 0.51 | 1.07 | sunlamp, ~ 95°/4 hr[d] | I-A | >0.3(>0.3->0.6) | at most trace |
| 138 | 6.20 | Ph₃GeGePh₃[c] | 0.54 | 1.06 | 0.068 mmole (Bu$^t$O)₂, 130°/1 hr | I-D | 2.0(2.0–4.0) | trace |
| 139 | 5.64 | | 0.50 | 0.99 | sunlamp, ~ 95°/1 hr | I-A | trace | trace |
| 140 | 5.49 | | 0.16 | 0.33 | sunlamp, ~ 98°/8 hr[d] | I-A | > trace | at most trace |

[a]See footnote a of Table II; Numbers in parentheses result from excluding from the calculation any formaldehyde in excess of the molal amount of germanium compound; this probably represents the limiting stoichiometry of formation of pro-glycol.
[b]Work-up all II-B
[c]Not highly soluble in benzene.
[d]Progress of reaction monitored.

lows.

Derivatization of Glycol from Hydrolyzed Product

The denser phase (0.60 g, containing 0.25 mmole of glycol) from the work-up of Example 131 was treated as described in D3 above to yield 15 mg. of precipitate which was recrystallized from hexane to give product of mp 62°-8° whose vpc retention time agreed with that of ethylene glycol dibenzoate and whose nmr spectrum contained absorptions attributable to ethylene glycol dibenzoate.

EXAMPLES 141–142

In accordance with these examples triphenylsilane and α-polyoxymethylene were reacted in benzene solvent at various temperatures and reaction times. The reaction products were then hydrolyzed following Procedure II-B. The amount of the reactants and solvents, the reaction conditions, variations in procedure, and the results of these examples are given in the Table XIII which follows.

EXAMPLES 152–155

In accordance with these examples $(Bu_2Sn)_x$ and

TABLE XIII.

| | | Reaction of Triphenylsilane and α-Polyoxymethylene | | | | | |
|---|---|---|---|---|---|---|---|
| | | Reactants, mmoles | | | Procedure[d] | Overall % Conversion[a,b] to | |
| Example | Solvent, mmoles | Ph₃SiH | CH₂O | Reaction Conditions | Reaction | Methanol | Glycol |
| 141 | Benzene, | 5.44 | 0.56 | 1.00 | 130°/1 hr | I-C | ≧3(≧3–≧5) | ≧4(≧4–≧7) |
| 142 | | 6.02 | 0.50 | 1.15 | sunlamp, ~ 95°/21 hr[c] | I-A | ≧2(≧2–≧4) | trace |

[a] See footnote a of Table II; For Bu₂Sn, read Ph₃SiH.
[b] Products identified from nmr spectrum only.
[c] Progress of reaction monitored.
[d] Work-up all II-B.

EXAMPLES 143–151

There are advantages attendant to the in situ generation of catalysts, particularly sensitive ones. In the present reaction, such a procedure could apply both to the reaction step and to the step in which glycol is freed from pro-glycol by reaction, for example, with $R_2SnH_2$. Should the compound containing, for example, the tin which results from production or consumption of pro-glycol be an acceptable tin-containing precursor of the in-situ-generated tin compound(s), the elements of the continuous "one pot" generation and regeneration of catalyst could be in hand. The reactions of $Bu_3SnH$ (cf. Table X) produced [K. Hayashi, J. Iyoda, and I. Shiihara, J. Organometal. Chem., 10, 81 (1967); G. L. Grady and H. G. Kuivila, J. Org. Chem., 34, 2014 (1969); J. Lipowitz and S. A. Bowman, Aldrichim. Acta, 1 (1973)] by the reaction of bis (tributyltin) oxide with polymethylhydrosiloxane, viz.,

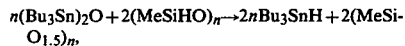

$n(Bu_3Sn)_2O + 2(MeSiHO)_n \rightarrow 2nBu_3SnH + 2(MeSiO_{1.5})_n$, tested part of these ideas.

In accordance with these examples $(Bu_3Sn)_2O$, (MeSiHO), and mixtures thereof were reacted with α-polyoxymethylene in benzene solvent at various temperatures and reaction times. The reaction products were then hydrolyzed following Procedure II-B. The amount of the reactants and solvent, the reaction conditions, variations in procedure, and the results of these examples are given in the Table XIV which follows.

$Bu_3SnH$ were reacted with a mixture of acetaldehyde and α-polyoxymethene in benzene solvent at various temperatures and reaction times. The reaction products were then hydrolyzed following Procedure II-B. The amount of the reactants and solvent, the reaction conditions, variations in procedure, and the results of these examples are given in the Table XV which follows.

Derivatization of Propylene Glycol and 2,3-Butanediol from Product(s) of the Reaction Group IV Catalysts with Formaldehyde and Acetaldehyde. Typical Procedures 1. Propylene glycol (100 μl) was treated as described for ethylene glycol in section D3. A denser, viscous layer was produced which was washed with 2×1.65 ml of water and pumped dry to give 33 mg. of product. Nmr (CDCl₃): tau = 1.7–2.8 (m, 9.6H), 3.8–4.0(m, 0.88), 5.49 (d,2.0H), 8.52(d,3.0H). A spectrum of a mixture of this product with $BzOCH_2CH_2OBz$ was qualitatively identical to the original except for an additional singlet at tau = 5.32.

2. Similar treatment of 100 μl of 2,3-butanediol (Aldrich, stated bp 180°–3°) produced no separate phase, even after concentration and prolonged refrigeration. It would be anticipated, therefore, that 2,3-butanediol would not be isolatable from a $CH_2O/CH_3CHO$ reaction mixture by use of this procedure.

3. The reaction from the work-up of example 154 was treated as described in section D3 to give a total of 62 mg of products whose nmr spectra and vpc's (⅛"×10' 20°/. OV-17 on DMCS-treated chromosorb W) indicated the presence of ethylene glycol dibenzoate and propylene glycol dibenzoate.

TABLE XIV.

| | | Reaction of Bis(tributyltin) oxide/polymethylhydrosiloxane and α-Polyoxymethylene | | | | | | |
|---|---|---|---|---|---|---|---|---|
| | Solvent, | Reactants mmoles | | | | Procedure[b] | Overall % Conversion[a,b] to | |
| Ex. | mmoles | (Bu₃Sn)₂O | (MeSiHO) | CH₂O | Reaction Conditions | Reaction | Methanol | Glycol |
| 143[d] | Benzene, | 5.46 | 0.27 | 0.48 | 1.13 | sunlamp, ~ 97°/1.5 hr[c] | I-A | 43(51–102) | 22(26–52) |
| 144 | | 5.52 | — | 0.51 | 1.23 | sunlamp, ~ 97°/1 hr | I-A | >1.2(>1.4–>1.9) | 0 |
| 145 | | 5.63 | 0.28 | — | 1.09 | sunlamp, ~ 97°/1 hr | I-A | >2.1(>2.1–>4.1) | 5.1(5.1–10) |
| 146[e] | | 5.30 | 0.27 | 0.50 | 1.00 | 130°/2 hr | I-C | >22(>22–>44) | trace |
| 147 | | 10.1 | — | 0.91 | 1.73 | 130°/2 hr | I-C | 13(13–25) | 0 |
| 148 | | 5.55 | 0.27 | — | 1.00 | 130°/2 hr | I-C | 26(26–48) | 0 |
| 149[f] | | 5.29 | 0.27 | 0.47 | 0.97 | 0.073 mmole (Bu$^t$O)₂,130°/1 hr | I-D | >24(>25–>50) | 25(26–52) |
| 150 | | 6.49 | — | 0.54 | 1.07 | 0.062 mmole (Bu$^t$O)₂,130°/1 hr | I-D | >3.7(>3.7–>7.4) | 12(12–24) |
| 151 | | 5.37 | 0.29 | — | 1.10 | 0.068 mmole (Bu$^t$O)₂,130°/1 hr | I-D | 24(24–45) | 5.5(5.5–10) |

[a] See footnote a of Table II; For Bu₂Sn, read (Bu₃Sn)₂O/(MeSiHO). Based on either (Bu₃Sn)₂O or (MeSiHO), depending on which was the limiting reagent, in cases where both materials were used.
[b] Work-up all II-B
[c] Progress of reaction monitored
[d] cf. example 119 in Table X
[e] cf. example 122 in Table X
[f] cf. example 125 in Table X

TABLE XV.

Cross - Reaction of Acetaldehyde and α-Polyoxymethylene

| Ex. | Solvent, mmoles | Reactants, mmoles | | | Reaction Conditions | Procedure[b] | | Methanol | Glycol | Products, mmoles | |
|---|---|---|---|---|---|---|---|---|---|---|---|
| | | Tin Compound | $CH_2O$ | $CH_3CHO$ | | Reaction | | | | Propylene Glycol | 2,3-Butanediol |
| 152 | Benzene, 4.21 | $Bu_2Sn$, 0.95 | 0.92 | 1.11 | sunlamp, ~ 33°/7 hr[a] | I-A | | trace | trace | very small amount | not determined |
| 153 | 4.40 | 0.76 | 1.10 | 1.03 | sunlamp, ~ 98°/3 hr[a] | I-A | | >0.001[c] | ~0.22[ce] | ~ 0.05[e] | ~0.10[e] |
| 154 | 75.6 | 12.3 | 11.8 | 12.6 | sunlamp, ~ 98°/1-2 hr | I-A | | 0.022[c] | 2.2[e] | f | 1.7[e] |
| 155 | 5.18 | $Bu_3SnH$, 0.92 | 1.13 | 0.98 | 0.090 mmole $(Bu^tO)_2$, 130°/1 hr | I-D | | >0.08[c] | 0.19[c] | trace | trace |

[a]Progress of reaction monitored
[b]Work-up of all II-B
[c]Quantitative nmr analysis
[e]Quantitative vpc analysis
[f]Detected, but not determined.

EXAMPLES 156-159

In accordance with these examples $(Bu_2Sn)_x$ and formalin were reacted at various temperatures and reaction times in order to determine whether crude, commercial formalin can be used in the practice of this invention. In addition to being another, common source of formaldehyde, formalin is an aqueous solution, thus having the potential of effecting in situ hydrolysis of any pro-glycol produced.

The reaction products were then either analyzed without being reacted further or were hydrolyzed following Procedure II-B. The amount of the reactants and solvent, the reaction conditions, variations in procedure, and the results of these examples are given in the Table XVI which follows.

TABLE XVI.

Reaction of $(Bu_2Sn)_x$ and Formalin

| Example | Solvent, mmoles | Reactants, mmoles | | Reaction Conditions | Procedure | | Overall % Conversion[a] to to Glycol |
|---|---|---|---|---|---|---|---|
| | | $(Bu_2Sn)$ | $CH_2O$ | | Reaction | Work-up | |
| 156 | Benzene, 4.74 + acetone, 7.07, + water, 6.27 | — | 1.17 | 0.055 mmole $(Bu^tO)_2$,130°/1 hr | I-D | II-B | very small amount |
| 157 | Benzene, 4.62, + acetone, 7.15, + water, 6.34 | 0.41 | 1.05 | 0.055 mmole $(Bu^tO)_2$,130°/1 hr | I-D | none | 3.0(3.8–7.7) |
| 158 | Benzene, 5.00, + acetone, 7.20, + water, 6.26 | — | 1.07 | sunlamp, ~ 98°/1 hr | I-A | none II-B | perhaps trace trace |
| 159 | Benzene, 4.62, + acetone, 6.80, + water, 6.32 | 0.38 | 1.08 | sunlamp, ~ 98°/1 hr | I-A | none | 21(30–60) |

[a]See footnote a of Table II

What is claimed is:

1. The process of producing ethylene glycol and/or 1,2-propylene glycol which comprises reacting a non-cyclic oxymethylene compound by the hydration or acetalization of formaldehyde with a compound containing one or more of silicon, germanium and tin bonded therein which functions as an addend in a photochemically or thermally induced radical reaction, to form a 1,2-dioxyethylene containing compound, and cleaving such 1,2-dioxyethylene containing compound to form the glycol thereof said non-cyclic oxymethylene compound being formed by the hydration or acetalization of formaldehyde.

2. The process of claim 1 wherein the non-cyclic oxymethylene compound is hydrated formaldehyde.

3. The process of claim 1 wherein the non-cyclic oxymethylene compound is polyoxymethylene.

4. The process of claim 1 wherein cleaving is effected by hydrolysis.

5. The process of claim 1 wherein the compound contains tin bonded therein and cleaving is effected by hydrostannolysis.

6. The process of claim 1 wherein cleaving is effected by hydrogenolysis.

* * * * *

UNITED STATES PATENT AND TRADEMARK OFFICE
CERTIFICATE OF CORRECTION

PATENT NO. : 4,283,578
DATED : August 11, 1981
INVENTOR(S) : Leonard Kaplan

It is certified that error appears in the above—identified patent and that said Letters Patent is hereby corrected as shown below:

Col. 1, line 27, "Rev. (B)" should begin a new paragraph.

Col. 1, line 39, "Ethylene" should begin a new paragraph.

Col. 7, line 31 "8Note" should read --[Note--.

Col. 7, line 34, "prpared" should read --prepared--.

Col. 9, line 2, "theexamples" should read --the examples--.

Col. 9, line 20, "indicaed" should read --indicated--.

Col. 11, line 48, "chromatorgraphic" should read --chromatographic--.

Col. 11, line 64, "ehtylene" should read --ethylene--.

Col. 12, line 30 et seq., remove comma (,) from formula.

Col. 12, line 65, "minte" should read --minute--.

Col. 13, line 43, "0.32" should read --0.31--.

Col. 14, line 10, delete bracket (]) at end of line.

Col. 15-16, Table II, Example 37, "Reaction Conditions" should be --150°/4 hr$^b$--.

Col. 17-18, Table IV, Example 69: Work-up II-B, in last column under "Glycol" heading, insert --0--.

UNITED STATES PATENT AND TRADEMARK OFFICE
CERTIFICATE OF CORRECTION

PATENT NO. : 4,283,578

DATED : August 11, 1981

INVENTOR(S) : Leonard Kaplan

It is certified that error appears in the above—identified patent and that said Letters Patent is hereby corrected as shown below:

Col. 19-20 and 21-22, Table VII, the 4th column heading should read --$Bu_3SnSnBu_3$--.

Col. 26, line 31 "(m,088) should read --(m,0.88H)--.

Col. 26, line 45, "°/." should read --%--.

Col. 27, lines 52-53, delete "by the hydration or acetalization of formaldehyde".

Signed and Sealed this

First Day of December 1981

[SEAL]

Attest:

Attesting Officer

GERALD J. MOSSINGHOFF

Commissioner of Patents and Trademarks